(12) United States Patent
Miller et al.

(10) Patent No.: US 6,627,664 B2
(45) Date of Patent: Sep. 30, 2003

(54) PERYLENEQUINONES FOR USE AS SONOSENSITIZERS

(75) Inventors: Gerald G. Miller, Spruce Grove (CA); J. William Lown, Edmonton (CA)

(73) Assignee: Altachem Pharma Ltd., Alberta (CA)

( * ) Notice: Subject to any disclaimer, the term of this patent is extended or adjusted under 35 U.S.C. 154(b) by 0 days.

(21) Appl. No.: 09/771,555

(22) Filed: Jan. 30, 2001

(65) Prior Publication Data

US 2002/0143066 A1 Oct. 3, 2002

(51) Int. Cl.⁷ .................. A61K 31/12; A61K 31/075; A61K 31/05

(52) U.S. Cl. .................. 514/680; 514/732; 514/717
(58) Field of Search .................. 514/680, 732, 514/717

(56) References Cited

FOREIGN PATENT DOCUMENTS

| WO | WO-9833470 A2 * | 8/1998 | |
| WO | WO-9930620 A1 * | 6/1999 | .......... A61K/49/00 |

* cited by examiner

Primary Examiner—Sreeni Padmanabhan
Assistant Examiner—S. Jiang
(74) Attorney, Agent, or Firm—Cahn & Samuels, LLP

(57) ABSTRACT

The invention is perylenequinones that are both sonosensitizers and photosensitizers, and their therapeutic use.

3 Claims, 9 Drawing Sheets a. HYPOCRELLIN B (HB)    b. HBBA-R2    c. HBEA-R1    d. HBDP-R1

PERYLENEQUINONES FOR USE AS SONOSENSITIZERS

TECHNICAL FIELD OF THE INVENTION

The invention involves compositions and methods for treating diseases and the like by administering compounds that are both photosensitizers and sonosensitizers.

BACKGROUND OF THE INVENTION

Treatment for cancer has traditionally encompassed three main strategies: surgery, chemotherapy, and radiotherapy. Although considerable progress in these areas has been attained, the search for more effective and safe alternative treatments continues. Lipson, et al. were the first to use photodynamic therapy (PDT), in 1966 at the Mayo Clinic [*Proc. IX Internat. Cancer Congress*, page 393 (1966)].

Since the advent of PDT, problems have been associated with photosensitizer use, including prolonged cutaneous phototsensitivity; the compositions are oligomeric mixtures of lipophilic molecules prone to molecular aggregation (with concomitant loss of photopotentiation); complicated pharmacokinetics; poor absorption and photoactivation in the "therapeutic window" (600 nm to 850 nm, i.e., visible red light). Furthermore, batch reproducibility, even in the clinical compositions, has been poor.

The photosensitizing properties of perylenequinonoid pigments (PQPs), such as hypocrellins, in biological systems have been recognized during the past two decades. See Diwu, et al., *J. Photochem. Photobiol. A: Chem.*, 64:273 (1992); Zhang et al., (1989); and Wan, et al., "Hypocrellin A, a new drug for photochemotherapy," Kexue Tongbao (English edition) 26:1040 (1981).

Perylenequinones comprise a growing and highly diverse group of natural pigments, and they posses some unique chemical and biological properties. The natural perylenequinonoid pigments (PQP) identified to date include hypocrellins, cercosporin, phleichrome, cladochrome, elsinochromes, erythroaphins, and calphostins. Most of them are produced by a wide variety of molds. For their general chemical properties [see Weiss, et al., *Prog. Chem. Org. Nat. Prod.*, 52:1 (1987) and Diwu, et al., *Photochem & Photobiol.*, 52:609–616 (1990)]. PQP's general photophysical and photochemical properties have been reviewed in Diwu, et al., *Pharmac. Ther.*, 63:1 (1994). Hypocrellins belong to the general class of perylenequinonoid pigments, and include hypocrellin A (HA) and hypocrellin B (HB).

Because of the difficulty of collecting sufficient activated photosensitizer at the site of action, none of the previously known photosensitizers have gained widespread use as therapeutics.

The importance of sonodynamic therapy (SDT) lies ultimately in its similarity to PDT, an elegant and effective tumor treatment whose success is due to the use of light and drug in combination, i.e., two treatment elements, neither of which has toxic effects by itself (Marcus, 1992). PDT has mild side effects, destroys relatively little healthy tissue, and new photosensitizers with better therapeutic indices and improved clinical properties are being developed. The principal impetus for the development of SDT has been improvement upon PDT's dosimetric shortcomings. PDT is currently restricted to use with superficial tumors. Its use on tumors deep within the body requires interstitial irradiation that increases the complexity of the treatment and compromises its noninvasive nature. SDT provides a means to reach such tumors, since ultrasound propagates easily through several centimeters of tissue, and like light, can be focused principally on the tumor mass where it activates the sonosensitizing compound. Targeted SDT offers the possibility of improving the tolerance of this therapy by further restricting its effects to the target tissue.

While these discoveries represent significant advances, two serious deficiencies remain in the development of experimental SDT. A substantial problem is the lack of sonodynamic agents with favorable clinical properties. Porphyrins are known to cause significant cutaneous photosensitivity (Estey et al., 1996), doxorubicin is cardiotoxic (Myers et al., 1976), and DMSO, DMF and MMF are hepatotoxic (Misik and Riesz, 1996). New sensitizers with better sonodynamic properties, which have milder side effects and which are rapidly cleared, would greatly improve the clinical application of SDT. A further problem is the lack of standardization in the conditions used for evaluating sonodynamic agents.

Potential sonodynamic agents have been tested following exposure to ultrasound intensities ranging from 0.25W/cm$^2$ to 40W/cm$^2$, and frequencies from 500 MHz to 1 MHz (Harrison et al., 1991; Sasaki et al., 1998). Though in vivo use would seem to require greater energies due to roughly isotropic dissipation of the ultrasonic energy, little effort has been made to compare experimental conditions in vitro with those in vivo. Where one group will find evidence of sonodynamic effect, different investigators do not under apparently similar conditions. Development of standard insonation and assay systems compatible with clinical use will permit a more rigorous assessment of the sonodynamic effects of current and future sonosensitizers.

Sonodynamic activation of sensitizers has been found to be useful since ultrasound has the appropriate tissue attenuation coefficient for penetrating intervening tissues to reach desired treatment volumes, while retaining the ability to focus energy on reasonably small volumes. Diagnostic ultrasound is a well accepted, non-invasive procedure widely used in the developed world, and is considered safe even for fetal imaging. The frequency range of diagnostic ultrasound lies between 100 kHz–12 MHz, while 50 kHz sound provides enough energy to effect cellular destruction through microregional cavitation.

Sonodynamic therapy provides treatment strategies unavailable in standard photodynamic therapy, due to the limited tissue penetration of visible light. One example would be the treatment of newly diagnosed breast cancer, where local and regional spread of micrometastatic disease remains clinically undetectable. Using immunoconjugates (anti-breast cancer Mab—sonosensitizer hybrids), it would be theoretically possible to selectively eradicate micrometastases in the absence of normal tissue damage.

Beyond these basic properties shared with other waves, ultrasound exhibits unique properties when propagating through water. Above a certain threshold intensity, propagation of ultrasound waves through water elicits an effect termed 'cavitation' (Rayleigh, 1917; Connolly and Fox, 1954). Cavitation involves the formation of small bubbles or 'cavities' in the water during the rarefaction half of the wave cycle, followed by the collapse of these bubbles during the compression half of the cycle (Putterman, 1995). Cavities focus the energy of the incident ultrasonic radiation by many orders of magnitude (Hiller et al., 1992). The consequence is that regions of cavitation in water are sites of extremely high temperature and pressure. Estimates of the temperatures generated in a collapsing cavity range from 5000K to 10⁶K (Suslick et al. 1986; Flint and Suslick, 1991; Misik and Riesz, 1995; Kaiser, 1995).

The biological effects of exposure to ultrasound are the result of its physical and chemical effects. The most obvious biological effects of ultrasound treatment stem from heating of the medium through which it passes. Such heating is exploited during physiotherapy to help heal injured tissues. (Lehmann et al., 1967; Patrick, 1966), and has been investigated as a possible modality for tumor treatment. This is due to the sensitivity of many tumours to hyperthermia, a state in which tissue temperatures are elevated above 42° C. (Doss and McCabe, 1976; Marmor et al., 1979; Sculier and Klastersky, 1981; Bleehen, 1982; Hynynen and Lulu, 1990). Ultrasound has also been used in combination with radiation therapy to improve treatment response in vivo compared to radiotherapy alone (Clarke et al., 1970; Repacholi et al., 1971; Mitsumori et al., 1996). A principal danger in the use of ultrasound for therapeutic purposes is the formation of 'hotspots' due to regions of constructive interference and preferential absorption of ultrasonic energy by bone regions with low curvature radii[†] (Lehmann et al., 1967; Linke et al., 1973). These hotspots can cause serious damage to nearby tissues (Hill, 1968; Bruno et al., 1998).

As is the case of hematoporphyrin derivatives, natural PQPs do not themselves exhibit absorptivity longer than 600 nm, a characteristic that inherently predicts a decreased capability of activation as tissue depth increases beyond 3–5 mm. This means that the natural PQPs are not sufficiently strong for photodynamic therapy, and this limits their photodynamic therapy applications.

Deficiencies of current porphyrin and PQP photosensitizers for photodynamic therapy have stimulated the development of a series of second generation compounds which have improved properties with respect to light absorption in the red spectral range, purity, pharmacokinetics, and reduced cutaneous photosensitivity. These deficiencies also lead to investigating other forms of activating the sensitizer, e.g., activation using sound waves.

SUMMARY OF THE INVENTION

In accordance with the present invention, derivatives of perylenequinone pigments (PQPs) having both photosensitizing properties and sonosensitizing properties are used to treat diseases and other conditions. Moreover, the PQP derivatives of the present invention may be conjugated to a delivery moiety to enhance the ability of the PQP derivative to target pre determined cells or structures in vitro or in vivo.

The methods and compositions of the present invention, activated by light and/or sound, exhibit substantial absorption in the red spectral region or therapeutic frequencies of ultrasound; produce high singlet oxygen yield; can be produced in pure, monomeric form; may be derivatized to optimize properties of red light absorption, ultrasound activation, tissue biodistribution, and toxicity; have reduced residual cutaneous photosensitivity; and are rapidly excreted. They afford nuclear targeting by covalent attachment to DNA minor-groove binding agents, such as stapled lexotropins, to enhance phototoxicity. They are not genotoxic. This trait is important in the context of treatment-related secondary malignancies. Conjugation with transferrin affords specificity with respect to the treatment of a variety of diseases, including ovarian cancer and breast cancer. Conjugation with a bisphosphonate affords specificity with respect to the treatment of a variety of diseases, including any disease or condition that involves the bone matrix, e.g., bone metastases of breast and prostate cancer, or osteoporosis. Conjugation with a tumor binding peptide affords specificity with respect to the treatment of a variety of diseases, including those that involve specific cell surface carbohydrate antigens.

Many PQP properties are summarized in Diwu, et al., *J. Photochem. Photobiol. A. Chem.*, 64:273 (1992). Some perylenequinones are also potent inhibitors of certain viruses, particularly human immunodeficiency virus (HIV), and also the enzyme protein kinase C (PKC). Both anti-HIV and anti-PKC activities of certain PQPs are light-dependent, a phenomenon implicated in the photodynamic therapy of cancers [Diwu, et al., *Biochem. Pharmacol.*, 47:373–389 (1994)]. The Diwu et al paper also discloses the successful conjugation of HB to a protein.

The photosensitizing and sonosensitizing compounds of the present invention, when administered systemically, distribute throughout the body. Over a short period, ranging from hours to days, the compounds clear from normal tissues, but are selectively retained by rapidly proliferating cells (e.g., cancer cells or psoriasis lesions) for up to several days. The PQPs of the present invention are inactive and non-toxic until activated, e.g., exposed to light in a specific wavelength range or to sound in a specific frequency range.

The use of compounds that can be activated using two different activation protocols is therapeutically beneficial. Light, which can penetrate to a surface depth of about 5 mm to about 7 mm, can activate compounds for treating surface lesions or those target cells within a certain distance from a light source. Ultrasound, on the other hand, can penetrate deep within the body to treat deeply seated cells, such as tumor masses inaccessible to a source of light.

The compounds of the present invention are also beneficial therapeutically due to their dual selectivity. The compounds of the present invention are selective in their ability to preferentially localize the drug at the site of a predetermined target, such as a cancer cell, and they are selective in that precise delivery of light and/or sound can be confined to a specific area.

The methods and compositions of the present invention, when administered in vivo, such as intravenously, distribute throughout the body. In subsequent hours, and sometimes days, the compositions containing at least one perylenequinone derivative begin to clear from normal tissues, but are selectively retained for up to several days by hyperproliferating cells, such as cancer cells. The perylenequinone derivative remains inactive and non-toxic until it is activated. In accordance with the present invention, the perylenequinone derivative may be activated by light, by sound, or by light and sound. The hyperproliferating cells, now containing or contacted with a perylenequinone derivative, may be exposed to an activation source, e.g., light of an appropriate wavelength or sound of an appropriate frequency, or both. Exposing the site containing the hyperproliferating cells with the activation source permits selective activation of the retained perylenequinone derivative, which in turn initiates local necrosis or apoptosis in the hyperproliferating cell tissue leading to cell death.

In combination with the delivery system according to the present invention, the compositions and methods of the present invention permit increased selectivity by preferential localization of the perylenequinone derivative at the site of the targeted cells, and permit increased selectivity by confining the activation source to a specific area, e.g., light and/or sound confined to a discrete area.

MODES FOR CARRYING OUT THE INVENTION

Figure 1:
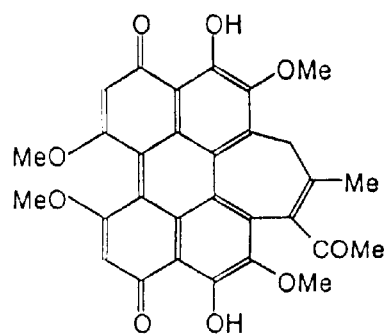
FIG. 1 shows the structures for naturally occurring hypocrellin (FIG. 1A), and exemplary synthetic derivatives, HBBA-R2 (FIG. 1B), HBEA-R1 (FIG. 1C), and HBDP-R1 (FIG. 1D).
Figure 1:
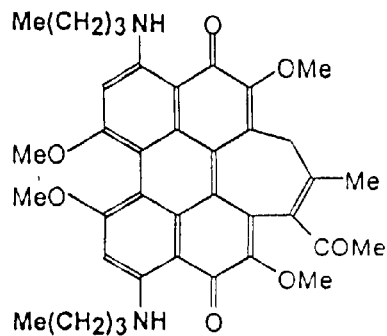
Figure 1:
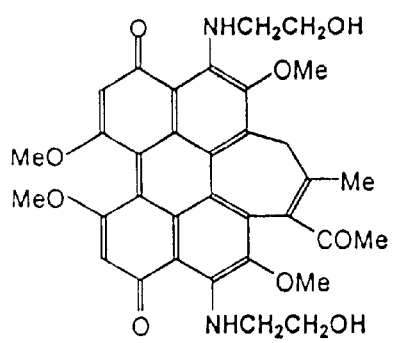
Figure 1:
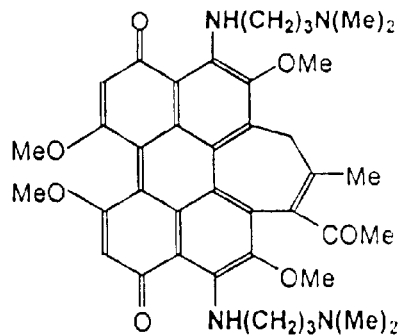

The present invention comprises the use of perylenequinone (PQP) derivatives as photodynamic and sonodynamic agents, and the use of the derivatives according to the invention as therapeutics.

The present invention includes a composition and method for treating a pre-determined disease or condition comprising administering a therapeutic amount of a composition comprising a perylenequinone derivative, allowing the perylenequinone derivative to distribute to a portion of the body, preferably throughout the body, and activating the perylenequinone derivative in an area containing hyperproliferating cells. In preferred embodiments of the invention, the administering step includes administering a perylenequinone derivative conjugated to a delivery moiety, including but not limited to transferrin, a bisphosphonate compound, and a tumor binding peptide. In preferred embodiments of the invention, the activating step includes activating the perylenequinone derivative with light, with sound, or with both light and sound.

The present invention also includes methods and compositions that involve a PQP conjugated to transferrin or a portion thereof, the use of transferrin as a delivery system for delivering an active agent to a pre-determined site, and activating the conjugate. In preferred embodiments of the invention, the conjugate may be activated by light, ultrasound, or combinations thereof. In preferred embodiments of the invention, the conjugate may be useful in treating small cell lung cancer or other hyperproliferating cells.

The present invention also includes methods and compositions that involve the topical application of a composition according to the invention, and activating the active agent in the composition. In preferred embodiments of the invention, the active agent is suitable for treating dermatological conditions, including but not limited to acne and hair removal. In preferred embodiments of the invention, the conjugate may be activated by photoactivation, sonoactivation, or combinations thereof.

The present invention also includes methods and compositions that involve the use of a composition according to the invention as an anti-bacterial agent in dental applications. In these embodiments of the invention, the active agent is formulated into a liquid composition, such as a mouthwash, contacting a tooth or teeth with the composition, and activating the active agent in the composition. In this embodiment of the invention, the composition is useful in treating cariotosis and the like. In preferred embodiments of the invention, the conjugate may be activated by photoactivation, sonoactivation, or combinations thereof.

The invention also comprises a method of treating a disease by administering a therapeutically sufficient amount of at least one PQP derivative, and activating the derivative(s) using both photoactivation and sonoactivation. Typically, the PQP derivative may be activated by exposing the derivative to a pre-determined wavelength of light and a pre-determined sound frequency.

The invention also includes photosensitive and sonosensitive compounds that further comprise a cleavable linker, said linker being cleavable in vivo. In accordance with the present invention, the cleavable linker may be chosen to alter one or more properties of the compound, including but not limited to solubility, stability, absorption, and the like. Cleavable linkers include, but are not limited to, polyamides and sugars.

As used herein, "perylenequinone derivative" or "derivative" refers to all compounds derived from native or natural perylenequinones (PQPs) and which can be activated by light of a pre-determined wavelength and/or by sound of a predetermined frequency. In a preferred embodiment of the invention, the derivative is a compound derived from naturally occurring quinone compounds. A derivative according to the invention may also be complexed with or include other active reagents, including but not limited to chemotherapeutic agents or alkylating agents. Exemplary PQPs include, but are not limited to hypocrellins, cercosporin, phleichrome, cladochrome, elsinochromes, erythroaphins, and calphostins. As noted in more detail below, the composition containing a PQP active agent may include a wide variety of additional components, including, for example, one or more of gases, gaseous precursors, liquids, oils, stabilizing materials, diagnostic agents, photoactive agents, bioactive agents and/or targeting ligands.

In a preferred embodiment of the invention, the PQP is an amino acid derivative of hypocrellin B. At the present time, the most preferred immunoconjugates use hypocrellin B which include an acid, acid bromide, hydrazine, thiol, or primary amine antibody binding site.

The compounds of the present invention may be produced by any method that results in a purified or substantially purified compound, or in a compound that is useful as a photodynamic or sonodynamic agent. The compounds of the present invention may also form a composition comprising a cocktail of compounds, e.g., more than one compound. These methods are well known in the art, e.g., Liu, et al., "Synthetic studies in novel hypocrellin B derivatives," Tetrahedron, 49:10785 (1993); and Diwu, et al., Anti-Cancer Drug Design, 8:129–143 (1993).

In accordance with the present invention, the PQP derivatives may be functionalized, e.g., include reactive groups including but not limited to an acid, hydroxyl, an acid halide (preferably bromide), a hydrazine, a thiol, or a primary amine. The binding reagent may include reactive groups including but not limited to amino acids, such as cysteine, lysine, aspartic acid, glutamic acid and other dicarboxylic acid amino acids, and other tri- or poly-functional amino acid derivatives.

The perylenequinone derivatives of the present invention are particularly suited for therapeutic use because they exhibit absorption and phototoxic activity in the phototherapeutic window (about 560 nm to about 700 nm); exhibit excellent sonodynamic activity in a frequency range from about 1 MHz to about 3 MHz; are low molecular weight, typically from about 550 daltons to about 880 daltons); are available in pure monomeric form; exhibit rapid serum and skin clearance; have negligible cytotoxicity in vitro and in vivo; have excellent photopotentiation (e.g., two orders of magnitude), so the safety margin in use is excellent; phototoxicity is mediated through conventional type II reactions and Type I reactions (indicating utility for hypoxic tumor cells); are potent inhibitors of protein kinases; confer apoptotic cell death in vitro and in vivo; exhibit no genotoxicity; exhibit excellent tumor control; may be molecularly configured for targeted delivery; may be targeted to nuclear regions to further augment sono/phototoxicity; and the parent hypocrellins are amenable to site-specific modification, so that many derivatives may be formed, derivatives with varying degrees of photosensitizing and/or sonosensitizing characteristics.

In accordance with the present invention, the cleavable linker may further comprise at least two functional groups, a first functional group for binding an active compound, and a second functional group for binding a targeting moiety, such as a protein or a carbohydrate.

As used herein, "disease" refers to the management, diagnosis, and/or palliation of any mammalian (including human) disease, disorder, malady, or condition that can be treated by photodynamic therapy. "Disease" includes but is not limited to cancer and its metastases, such as skin cancer; growths or tumors, and their metastases; tumors and tumor cells, such as sarcomas and carcinomas, including solid tumors, blood-borne tumors, and tumors found in nasal passages, the bladder, the esophagus, or lung, including the bronchi; viruses, including retroviruses; bacterial diseases; fungal diseases; and dermatological conditions or disorders, such as lesions of the vulva, keloid, vitiligo, psoriasis, benign tumors, endometriosis, Barett's esophagus, Tinea capitis, and lichen amyloidosis.

As used herein, "administering" and "delivering" refers to any action that results in exposing or contacting one or more PQP derivatives with a predetermined cell, cells, or tissue, typically mammalian. As used herein, administering or delivering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

As used herein, activation, activating, or similar terms refers to the use of light waves and/or sound frequency to make a compound or portion of a compound more reactive. Any method for applying a light source and/or a sound source to a perylenequinone derivative may be used in accordance with the present invention, e.g., direct application, an ultrasound machine, focused ultrasound, high-intensity focused ultrasound, and illuminating endoscopy, to name a few.

Upon application of the appropriate light or sound, the sensitizers can chemically (e.g., through oxidation, reduction and the like) change into a form that is toxic to the surrounding tissue. For example, following excitation of a photosensitizer or a sonosensitizer to a long-lived excited triplet state, a targeted tumor is destroyed either by the highly reactive singlet oxygen species (a Type II mechanism) and/or by free radical products (a Type I mechanism) generated by quantum energy transfer. Major biological target molecules of the singlet oxygen species and/or free radical products include nucleic acids, enzymes and cell membranes. A secondary therapeutic effect of the present methods involves the release of pathophysiologic products, such as prostaglandins, thromboxanes and leukotrienes, by tissue exposed to the effects of activated photosensitizers. Thus, it will be apparent to one skilled in the art that careful targeting of the photoactive or sonoactive agents is of paramount importance to achieve therapeutic effects without eliciting toxemias.

In accordance with an embodiment of the present invention, activating a sensitizer using light and activating a sensitizer using sound may be used together since each of the individual procedures are complementary. That is, red, visible light suitable for activating a perylenequinone derivative is capable of penetrating into tissue or into a body from about 5 mm to about 7 mm, and sound suitable for activating a perylenequinone derivative is capable of fully penetrating into tissue or into a body.

As used herein, "photopotentiation factor" refers to the property of the compound(s) to exert light- or sound-mediated toxicity in excess of its (their) inherent unactivated toxicity. In a preferred embodiment of the invention, the activation factor may be calculated as the ratio of the $LD_{50}$ of cells treated without activation to the $LD_{50}$ of the cells treated with an activated compound (drug $LD_{50}$ divided by activated drug $LD_{50}$). Where the term "$LD_{50}$" has been used above, the term "$IC_{50}$" may be substituted, to address the bioassays that concern metabolic activity rather than the endpoint of lethality, loss of reproductive capability, or clonogenic death. The relative photoactivation efficiency of a compound may also be determined using a clonogenic assay, an assay that is well known to those skilled in the art.

In accordance with the present invention, a desirable PQP derivative is one that is non-toxic (or of low toxicity) at high drug concentrations without activation, i.e., without light (also referred to as "dark"), and/or without sound, and is toxic at low concentrations when light of the appropriate wavelength, or sound of the appropriate frequency, is applied. As is recognized by those skilled in the art, the most desirable compounds are those that provide a wide range of non-toxic doses in an unactivated state, as this characteristic provides an increased safety factor for the patient.

As used herein, physiologically acceptable fluid refers to any fluid or additive suitable for combination with a composition containing a PQP derivative. Typically these fluids are used as a diluent or carrier. Exemplary physiologically acceptable fluids include but are not limited to preservative solutions, saline solution, an isotonic (about 0.9%) saline solution, or about a 5% albumin solution or suspension. It is intended that the present invention is not to be limited by the type of physiologically acceptable fluid used. The composition may also include pharmaceutically acceptable carriers. Pharmaceutically accepted carriers include but are not limited to saline, sterile water, phosphate buffered saline, and the like. Other buffering agents, dispersing agents, and inert non-toxic substances suitable for delivery to a patient may be included in the compositions of the present invention. The compositions may be solutions, suspensions or any appropriate formulation suitable for administration, and are typically sterile and free of undesirable particulate matter. The compositions may be sterilized by conventional sterilization techniques.

In accordance with a method of the invention, the binding agent must be capable of binding a predetermined binding site or receptor, and may be administered to the patient by any immunologically suitable route. For example, the binding agent may be introduced into the patient by intravenous, subcutaneous, intraperitoneal, intrathecal, intravesical, intradermal, intramuscular, or intralymphatic routes. The composition may be in solution, tablet, aerosol, or multiphase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition that includes a binding agent according to the invention; and the treated blood or serum is returned to the patient. The invention should not be limited to any particular method of introducing the binding agent into the patient.

The compounds of the present invention may be produced by any method that results in a purified or substantially purified compound, or in a compound that is useful as a photodynamic agent. The compounds of the present invention may also form a composition comprising a cocktail of compounds, e.g., more than one compound. These methods are well known in the art, e.g., Liu, et al., "Synthetic studies in novel hypocrellin B derivatives," Tetrahedron, 49:10785 (1993); and Diwu, et al., Anti-Cancer Drug Design, 8:129–143 (1993).

Intracellular uptake may be rapid (e.g., within about 2 hours), or uptake may require more time (e.g., about 20 hours or more). Some degree of selective tumor uptake might be achieved by modification of the pKa of the sensitizer, since the interstitial milieu of some tumors is more acidic than that of normal tissues. This invention includes a method for identifying compounds where the toxicity of the compounds is higher for cancer cells than for normal cells, via comparative clonogenic assays.

The PQP derivatives of the present invention may also be used in conjunction with and conjugated to a number of other compounds, signaling agents, enhancers, and/or targeting agents. For example, a hypocrellin derivative of the present invention may be conjugated to an antibody, preferably a monoclonal antibody. In accordance with the present invention, the binding agent includes any DNA minor-groove targeting agent, such as lexotropsin or netropsin, preferably to enhance the toxicity through targeting the cell nucleus. Suitable enhancers include but are not limited to pKa modifiers, hypoxic cell radiosensitizers, and bioreductively activated anti-neoplastic agents, such as mitomycin C (preferably to effect or potentiate the toxicity of the compound in hypoxic cells or microorganisms). Suitable signaling agents include but are not limited to markers of apoptotic cell death or necrotic cell death, or regulatory molecules endogenous to cell cycle control or delay, preferably to potentiate the phototoxicity or sonotoxicity of the compound(s) by induction of apoptotic or necrotic cell death, or by inhibition of the repair of any form of lethal or potentially lethal damage (PLD).

As noted above, an embodiment of the invention includes binding agent-PQP conjugates (or immunoconjugates) and the therapeutic use of these conjugates. In accordance with the present invention, any method of linking a binding agent to a PQP may be used. For example, it is well known how to link an antibody or an antibody fragment to a photosensitizer. For example, Goff, et al., British Journal of Cancer, 74:1194–1198 (1996) discloses the production of an immunoconjugate by incubating a photosensitizer with monoclonal antibody OC125, an antibody that specifically binds to the CA125 antigen associated with most ovarian cancers. In this exemplary immunoconjugate, polyglutamic acid may be bound to a monoethylendiamine monoamide derivative, which is then covalently linked to the carbohydrate moiety at the hinge region of the monoclonal antibody away from the antigen binding sites. Other exemplary linkages are disclosed in U.S. Pat. Nos. 4,722,906 and 3,959,078, both incorporated herein by reference. Briefly, these patents disclose providing a photosensitizer with a selector group, or a latent reactive group, that is the other member of a specific binding pair, e.g., a reactive group that covalently bonds to an antibody.

In accordance with the present invention, the PQP derivatives may be functionalized, e.g., include reactive groups including but not limited to an acid, hydroxyl, an acid halide (preferably bromide), a hydrazine, a thiol, or a primary amine. The binding reagent may include reactive groups including but not limited to amino acids, such as cysteine, lysine, aspartic acid, glutamic acid and other dicarboxylic acid amino acids, and other tri- or poly-functional amino acid derivatives.

As is recognized by one skilled in the art, an effective dose of the derivative or a conjugate that includes the derivative will depend in part on the severity of the disease and the status of the patient's immune system. One skilled in the art will recognize that a variety of doses may be used, and are dependent on a variety of well-known factors. Generally, the composition will include about 0.1 $\mu$g to about 2 mg or more of binding agent per kilogram of body weight, more commonly dosages of about 200 $\mu$g per kilogram of body weight. The concentration usually will be at least about 0.5%. Any amount may be selected primarily based on fluid volume, viscosity, antigenicity, etc., in accordance with the chosen mode of administration.

Administration of the conjugate or the derivative may be more than once, preferably three times over a prolonged period. As the compositions of this invention may be used for patients in a serious disease state, i.e., life-threatening or potentially life-threatening, excesses of the binding agent may be administered if desirable. Actual methods and protocols for administering pharmaceutical compositions, including dilution techniques for injections of the present compositions, are well known or will be apparent to one skilled in the art. Some of these methods and protocols are described in *Remington's Pharmaceutical Science*, Mack Publishing Co. (1982).

In accordance with another embodiment of the invention, a composition of the present invention may be administered alone, in combination with other compositions, or in sequence with other PDT compositions. These features afford potential augmentation of the photodynamic therapeutic ratio through sequential sensitizer administration (followed by light treatment). Under these conditions, a larger number of organelles can be targeted.

In this embodiment of the invention, a PDT method comprises administering a first photodynamic agent, preferably having a slow uptake, and administering a second photodynamic agent, preferably having a more rapid uptake than that of the first agent. Both first and second photodynamic agents may then be activated by exposing the patient and/or the agent to light of suitable frequency, as described above.

The excellent fluorescence properties of the hypocrellins and derivatives provide a valuable tool to monitor intracellular uptake and distribution kinetics by confocal laser scanning microscopy (CLSM). Each drug has unique properties of uptake and distribution (Miller et al 1995 a, b). The rate cells take up drug in humans in vivo and in vivo can be determined using similar protocols as Liu et al 1995 and Miller et al., 1995 a or b). In vivo, the ideal time between i.v. injection or administration of the drug and light administration is preferably when tumor concentration of the photodynamic agent is optimal with respect to normal tissues, typically up to about 24 hours, but as long as 48 hours or more (Table 2).

Some of the embodiments of the present invention also have the added benefit of functioning with or without the presence of oxygen. Therefore, some embodiments of the present invention are effective in the treatment of solid tumors which are either well oxygenated or either partially or fully hypoxic.

The photo- and/or sono-activating agents may be formulated for topical application in penetrating solvents or in the form of a lotion, cream, ointment or gel containing a sufficient amount of the photosensitizing agent compound to be effective for PDT therapy. Such topical formulations may be prepared in gel form by combining the photosensitizing agent with a solvent and adding a gelling agent thereto. Suitable gelling agents include carboxymethyl cellulose (Carbopol.TM. 934P from B. F. Goodrich of Brecksville, Ohio U.S.A.) and fumed silica (CAB-O-SIL.RTM., Cabot Corp., Tuscola, Ill.). The gelling agent is generally used in amounts of about 5–10 wt % to obtain a gel with the desired viscosity. Obviously, gels containing more or less gelling agent will have slightly higher or lower viscosity. One skilled in the art can readily obtain the desired gel viscosity by adjusting the concentration of gelling agent.

Additives, such as cosolvents, surfactants and/or bioadhesives frequently improve the gel properties and may be added as desired. Suitable cosolvents/surfactants include propylene glycol and glycerine. Suitable bioadhesives include carboxymethylcellulose, polyacrylic polymers, chitosan and sodium alginate, modified starch with polyacrylic polymers, eudispert hv hydrogels or xerogels, sodium hyaluronate, and polymers of polyethylene glycol, hydroxypropylcellulose, or carboxyvinyl. The additives may be incorporated into the gel by mechanically mixing the additives into a mixture of solvent and gelling agent.

Other additives may be used to enhance or maintain chemical stability and physiological suitability. Examples are antioxidants, chelating agents, inert gases, buffers and isotonicifiers. Examples of antioxidants and typical concentration ranges include acetone sodium bisulfite (0.1–0.8%), ascorbic acid (0.05–1.0%), monothioglycerol (0.1–1.0%), potassium metabisulfite (0.05–0.1%), propyl gallate (0.02%), sodium bisulfite (0.01–1.0%), sodium formaldehyde sulfoxylate (0.03–0.1%), sodium metabisulfite (0.02–0.25%), sodium sulfite (0.01–0.1%), sodium thioglycolate (0.05–0.1%).

Examples of chelating/complexing agents and typical concentration ranges include edetate sodium (0.005–0.1%), edetate calcium disodium (0.005%–0.01%), gentisic acid ethanolamide (1.0%–2.0%), niacinamide (1.0%–2.5%), sodium citrate (0.01%–2.5%), citric acid (0.001%–1.0%).

Buffers are used primarily to stabilize a formulation against the chemical degradation that might occur if the pH changed appreciably. Buffer systems employed normally have as low a buffer capacity as feasible in order to not disturb significantly the body buffer systems when injected. The buffer range and effect of the buffer on activity must be evaluated. Appropriate adjustment is useful to provide the optimum conditions for pH dependent partition into the target malignant tissues or lesion area. Examples of such buffer systems include the following acids: acetic, adipic, ascorbic, benzoic, citric, glycine, lactic, tartaric, hydrochloric, phosphoric, sulfuric, carbonic and bicarbonic; and their corresponding salts such as: potassium, sodium, magnesium, calcium and diethanolamine salts.

When the solution will be dispensed from multiple dose containers, antimicrobial agents in bacteriostatic or fungistatic concentrations are added in amounts effective to provide protection from bacteria or fungi. Among the compounds and concentrations most frequently employed are phenylmercuric acid (0.002–0.01%), thimerosal (0.01%), benzethonium chloride (0.01%), benzalkonium chloride (0.01%), phenol or cresol (0.5%), chlorbutanol (0.5%), benzyl alcohol (2.0%), methyl p-hydroxybenzoate (0.18%), propyl, p-hydroxybenzoate (0.02%), and ethylenediaminetetraacetic acid (EDTA).

Suitable penetrating solvents are solvents for the porphycene compound which will enhance percutaneous penetration of the porphycene compound. Solvents which have this property include proparacaine, dimethyl sulfoxide, dimethyl acetamide, dimethylformamide, 1-methyl-2-pyrrolidone, diisopropyladipate, diethyltoluamide and to a lesser extent propylene glycol. Additional solvents include substituted azacycloalkan-2-ones having from 5 to 7 carbons in the cycloalkyl group such as 1-dodecylazacycloheptan-2-one (AZONE) and other azacycloalkan-2-ones such as described in U.S. Pat. No. 3,989,816 incorporated herein by reference. Also included are N-bis-azocyclopentan-2-onyl alkanes described in U.S. Pat. No. 3,989,815 (hereby incorporated by reference), 1-substituted azacyclopentan-2-ones described in U.S. Pat. No. 3,991,203 (hereby incorporated by reference) and water-soluble tertiary amine oxides described in U.S. Pat. No. 4,411,893 (hereby incorporated by reference).

The topical formulations contain a sufficient amount of the photosensitizing compound to be effective in PDT therapy. Generally, concentrations in the range of 0.001 to 25 wt. %, preferably from about 1 to 5 wt. %, may be used.

The photosensitizing agents can be used with solvents and adjuvants appropriate to the photosensitizing agent chemistry to adjust the viscosity of the formulation. The most important solvents in this group are ethanol, polyethylene glycols of the liquid series and propylene glycol. A more comprehensive listing includes acetone, dimethyl acetamide, dimethyl formamide, dimethyl sulfoxide ethanol, glycerin, polyethylene glycol 300, and 400, propylene glycol, sorbitol, polyoxyethylene sorbitan fatty acid esters such as laureate, palmitate, stearate, and oleate, polyoxyethylated vegetable oil, sorbitan monopalmitate, 2-pyrrolidone; n-methyl-2-pyrrolidine; n-ethyl-1-pyrrolidine; tetrahydrofurfuryl alcohol, tween 80 and dimethyl isosorbide. Dimethyl isosorbide (ARLASOLVE.RTM. DMI, ICI Specialty Chemicals) has the advantage of being both water- and oil-soluble. Additionally, dimethyl isosorbide may be readily gelled with a gelling agent to produce gel formulations with, for example, 4% KLUCEL.RTM. (Hercules).

Additional topical formulations which may be used for the chosen photosensitizing agent are disclosed in U.S. Pat. Nos. 3,592,930 and 4,017,615 which are hereby incorporated by reference.

EXAMPLES

Example 1

Laser Light Wavelength and Dosage

Figure 7:
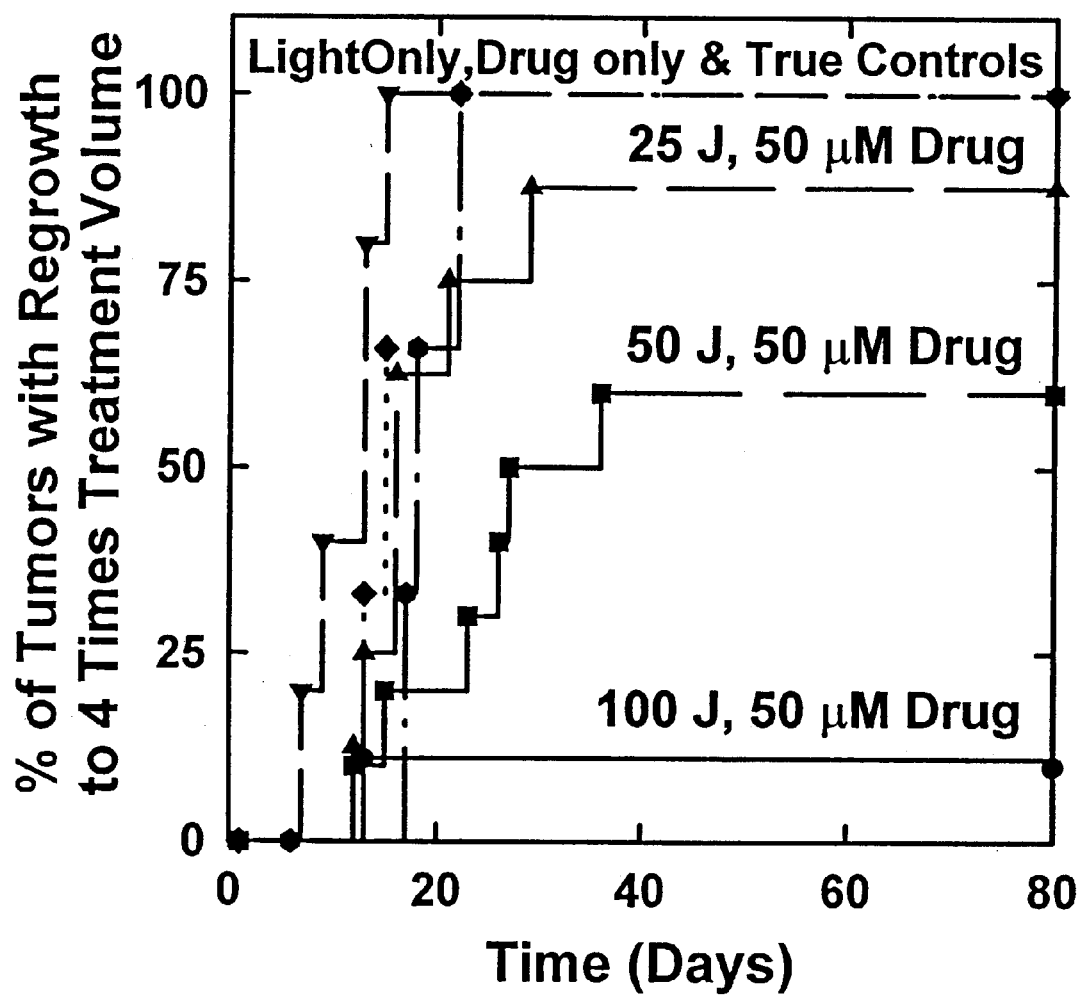
FIG. 7 shows EMT6/Ed tumor control in Balb/c mice following various doses of 630 nm light applied transcutaneously.
Figure 8A:
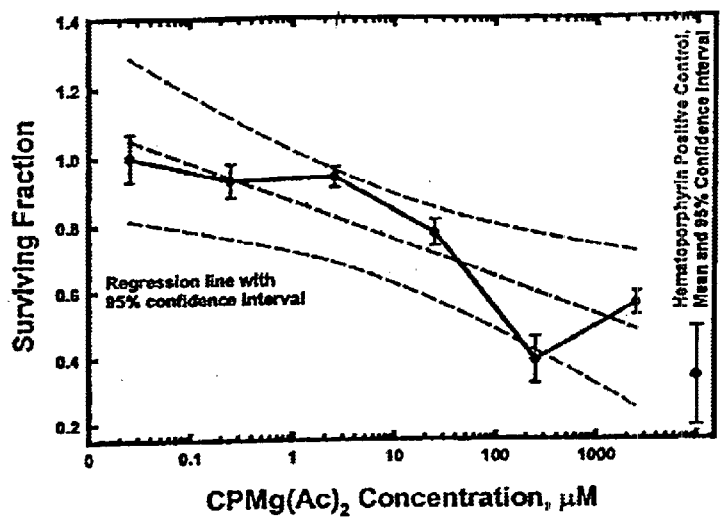
FIG. 8 shows the sonodynamic toxicity of two perylenequinone derivatives in human promyelocytic leukemia cells in vitro, with respect to a positive control, hematoporphyrin at 1 $\mu$M.
Figure 8A:
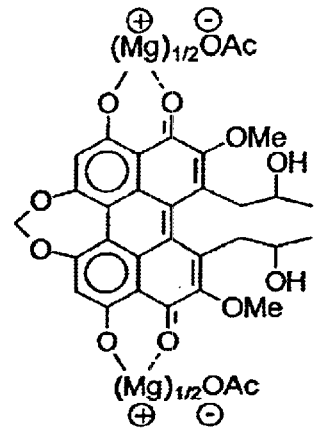
Figure 8B:
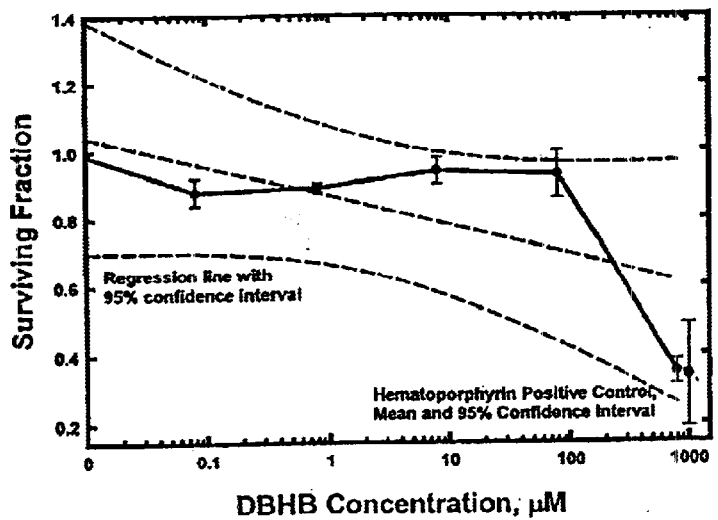
Figure 8B:
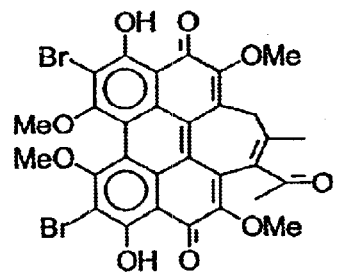
Figure 9:
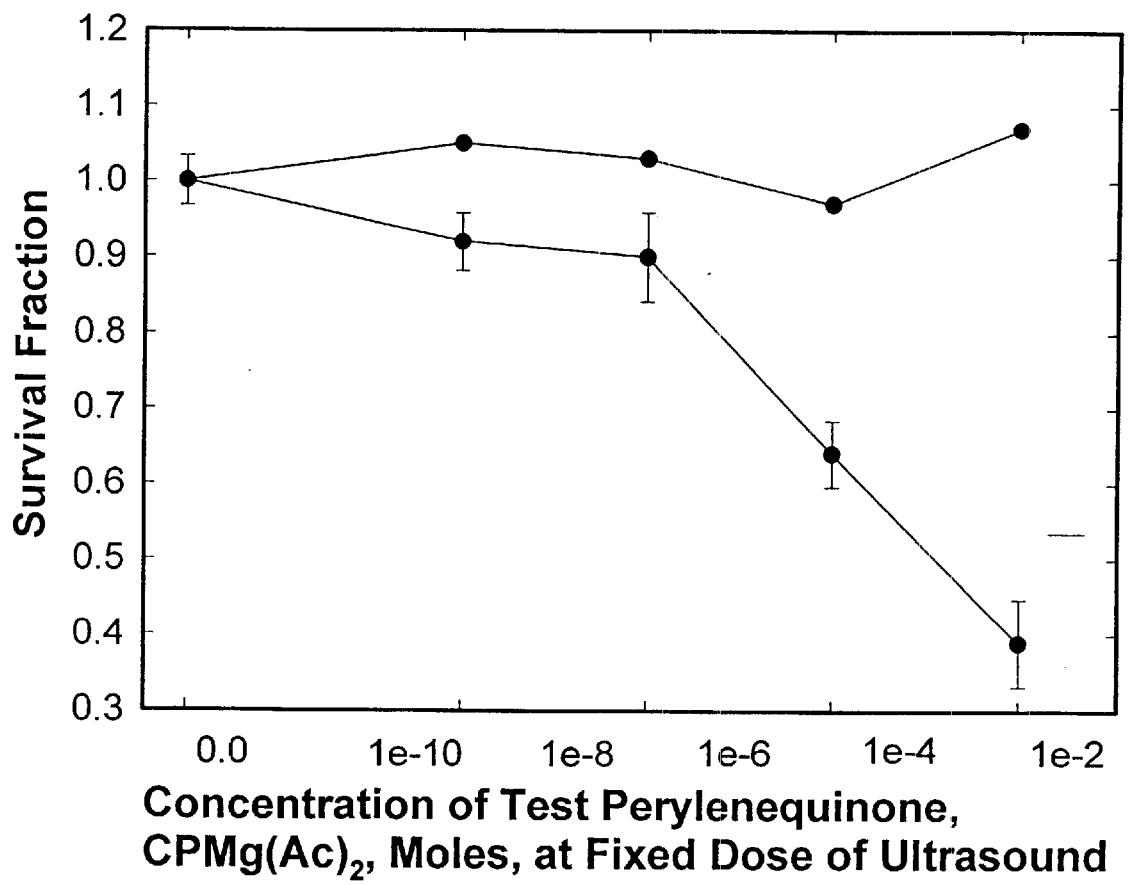
FIG. 9 shows evidence of sonodynamic killing of human leukemia cells using perylenequinone $C_{33}H_{28}O_{11}Mg$.

Both the concentration of drug and the dosage of light are important for treatment of tumors. Balb/c mice with EMT6/Ed tumors with 50 $\mu$mol/kg body weight of HBEA-R1 received various light dosages. The mice that received 100 Joules of 630 nm light (duration approximately 10 minutes) experienced approximately 90% tumor cure, mice that received 50 Joules of 630 nm of light experienced only a 40% cure rate and the cure rates were significantly lower at the lower light dosages (FIGS. 7 and 8).

Figure 3:
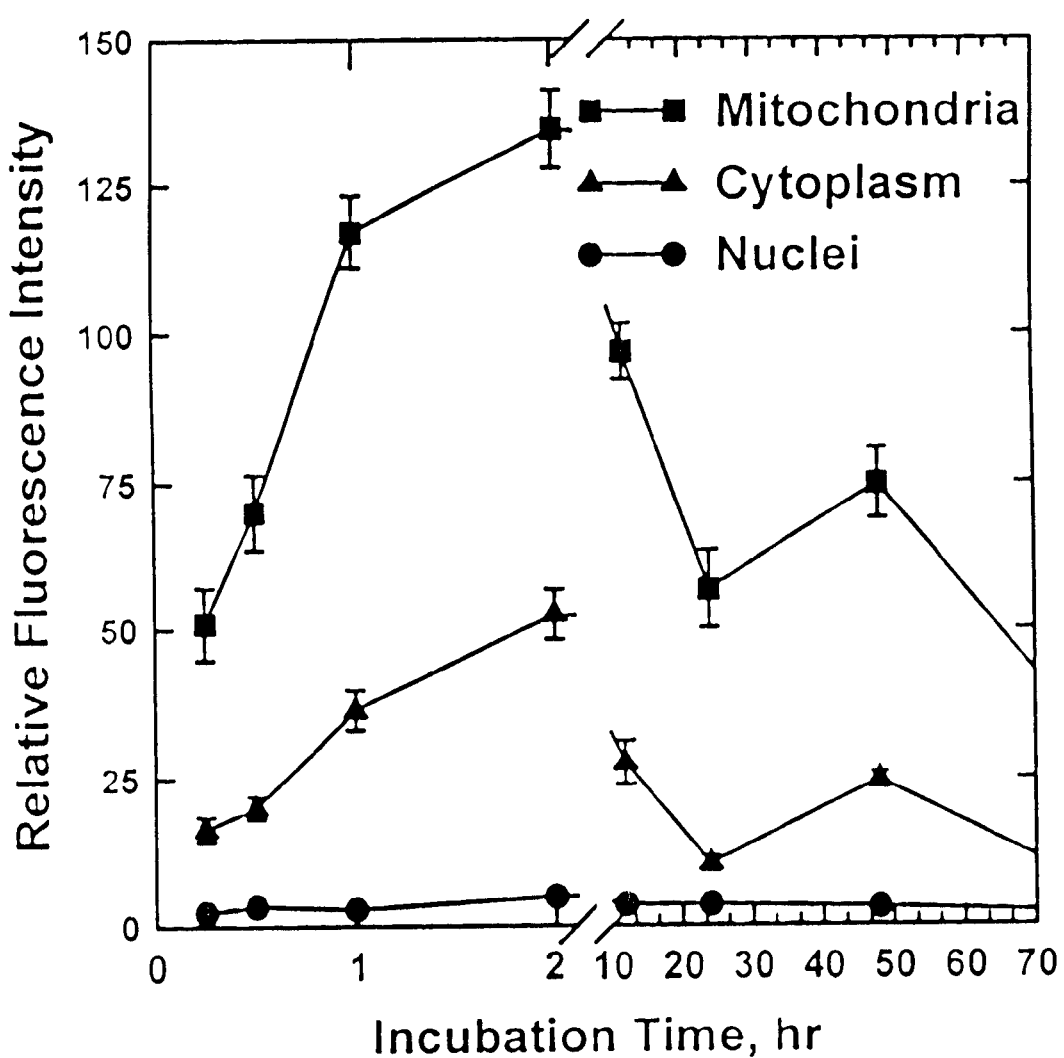
FIG. 3 shows the CLSM determination of uptake of HBEA-R1 under the same conditions employed for HB.

This invention provides a method for treating cancer which is enhanced in the presence of light wavelengths between 400 and 850 nm (see FIG. 3 and Table 1 for optimal wavelengths for individual compounds). The absorption spectra for many compounds are included in FIG. 3 and the main absorption peak for each compounds is included in Table 1. Many of these compounds have significant absorbance around the 630 nm (600 to 700 nm range) (Table 1). The optimal wavelength is different for each compound (Table 1). For HBEA-R1 and HBBA-R2 wavelengths between at least 630 and 688 nm are capable of killing cells. For deeper or larger tumors the longer wavelengths are preferred. For superficial tumors, laser wavelengths with lower wavelengths or wavelengths in the green spectrum would be more suitable to use (Nseyo et al., 1993) since the light does not penetrate as far. The ability of these compounds to be photopotentiated at higher wavelengths increases the size of tissue that can be treated with PDT and increases the depth at which treatment can be provided using PDT. Fiber optic probes can be utilized to direct the laser light. Light may also be delivered to a selected area, using an appropriate light source and shielding.

Figure 2:
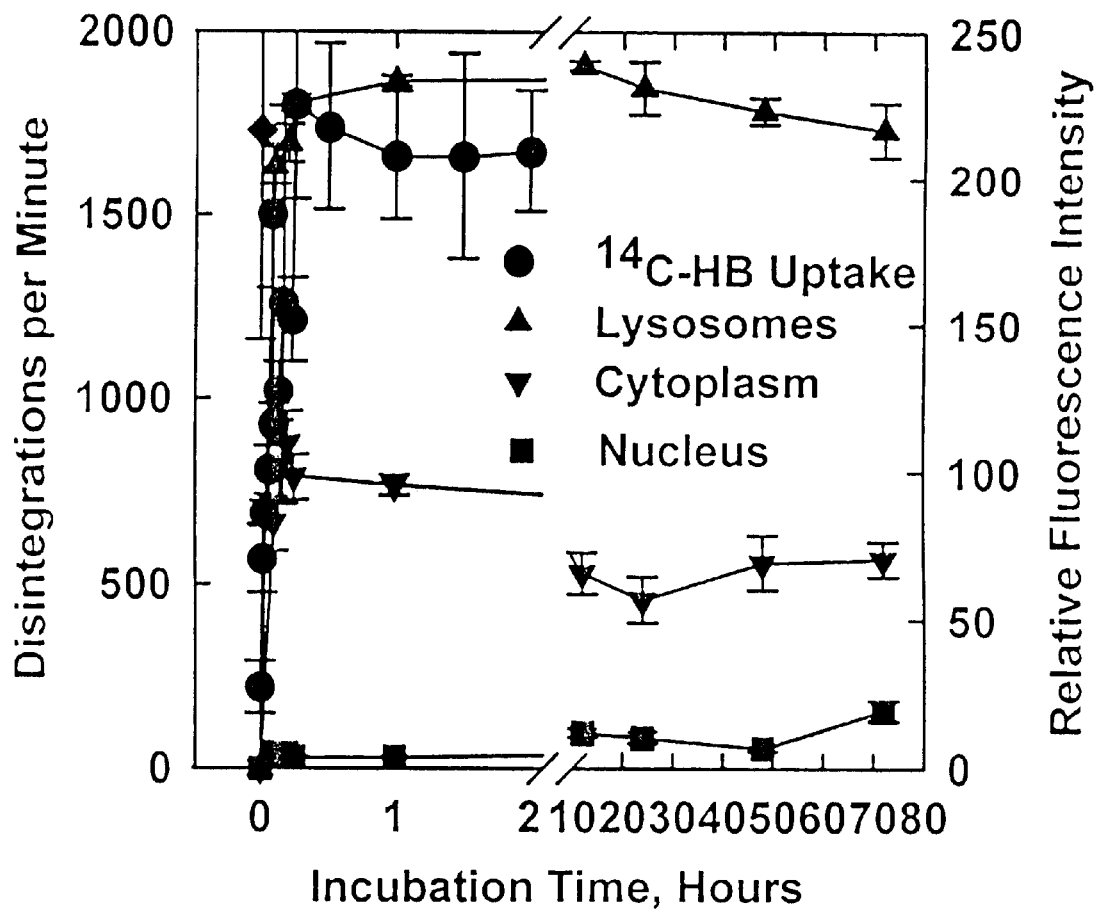
FIG. 2 shows the pharmacodynamics of HB in EMT6/Ed cells observed by $^{14}$C-labeling and confocal laser scanning microscopy(CLSM).

A method for treating bladder is described by Nseyo and associates (1993) this method can be applied using the compounds described in Table 1 or FIG. 2 and drug doses described and wavelengths described herein.

For applications of drug to a localized region or with identifiable target antigens there are several methods that are suitable for delivery, the delivery system are comprised of drug-liposome formulations, drug -monoclonal antibody delivery systems such as monoclonal antibody -liposome, or applied to exposed surfaces using a standard lipophilic skin cream. The drug can be applied topically or the route of delivery of the drug or drug and delivery system could be intravenous, intraperitoneally, intrathecally, intravesically, by intratumoral injection or by oral ingestion.

Example 2

The pharmacodynamics of HB in EMT6/Ed cells were observed by $^{14}$C-labeling and confocal laser scanning microscopy. The results are shown in FIG. 2. Cellular uptake reached equilibrium within 15 minutes of administration, implying saturation of intracellular binding sites. The extent and distribution of drug uptake remains stable for at least 72 hours of continuous incubation in the presence of drug, which under conditions employed was not cytotoxic.

Example 3

CLSM determination of uptake of HBEA-R1 under the same conditions employed for HB. The results are shown in FIG. 3. Uptake is complete within the first 2 hours, and intracellular concentrations diminish gradually during the following 70 hours.

Example 4

Figure 4:
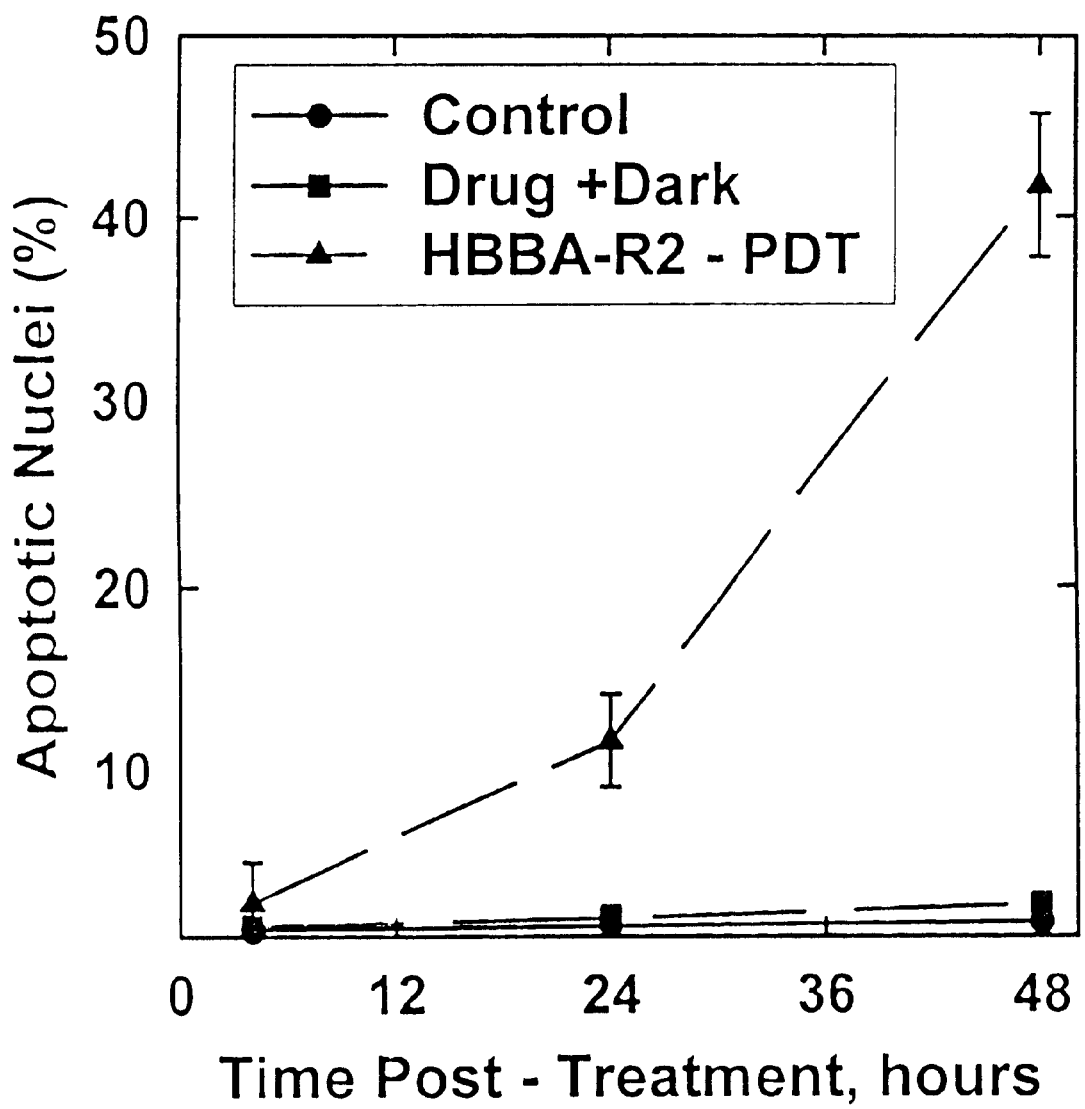
FIG. 4 shows propidium iodide determination of apoptotic nuclei in EMT6/Ed cells treated with HBEA-R1.

Propidium iodide determination of apoptotic nuclei in EMT6/Ed cells treated with HBEA-R1. The results are shown in FIG. 4. The background frequency of cells with apoptotic morphology is represented by the untreated control. Photosensitizing concentrations of the sensitizer do not induce apoptosis, however HBEA-R1 PDT results in 50% apoptotic morphology within 48 hours of treatment.

Example 5

Figure 5:
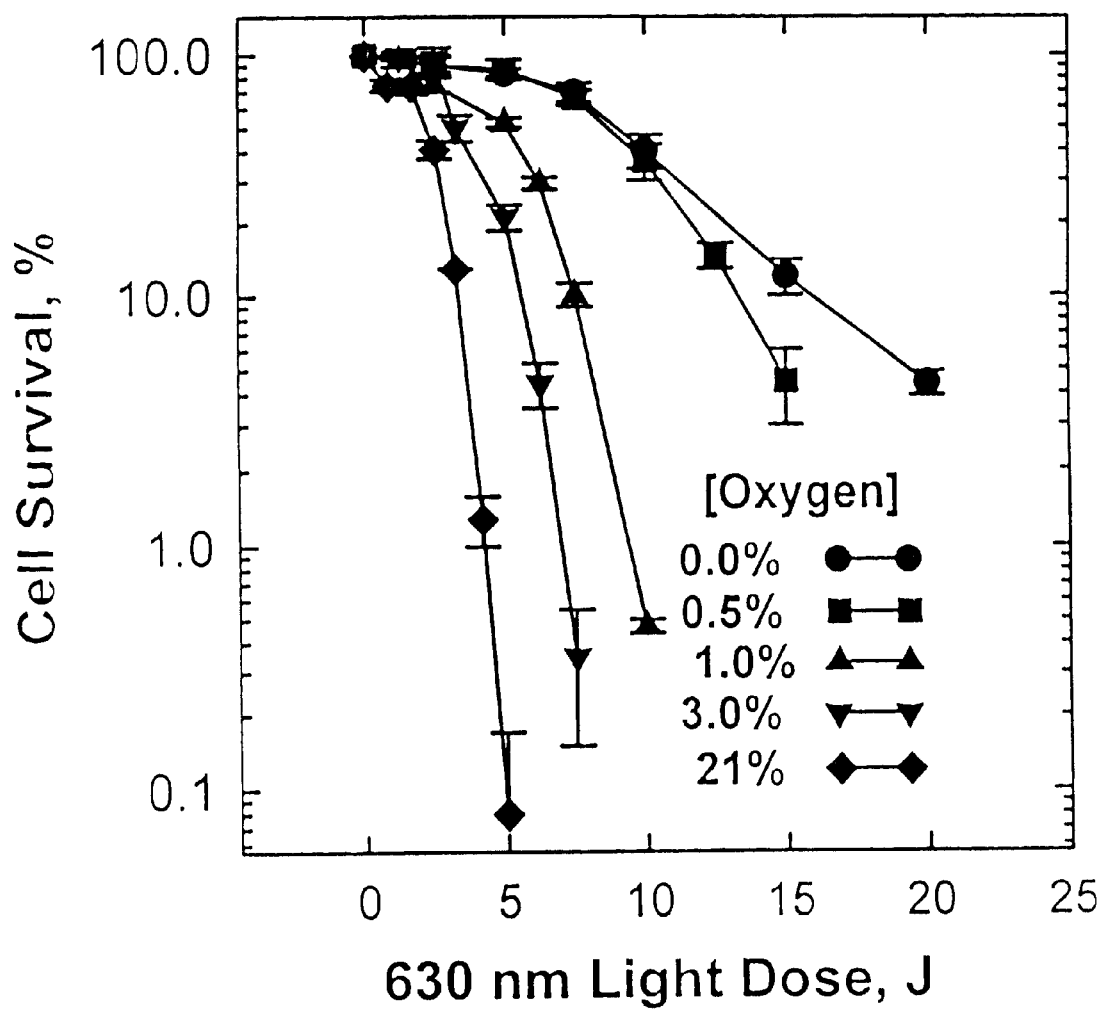
FIG. 5 shows the oxygen dependency of phototoxicity of HBEA-R1.

Oxygen dependancy of phototoxicity of HBEA-R1. The results are shown in FIG. 5. Phototoxicity diminishes as the $pO_2$ in the gas phase of the cell suspension is reduced for PDT treatment, from ambient to 0.0%. The oxygen enhancement ratio (O.E.R.) Is 4.0 at the $D_0$. Evidence of type 1—mediated phototoxicity is observed in the total absence of oxygen.

Example 6

Figure 6:
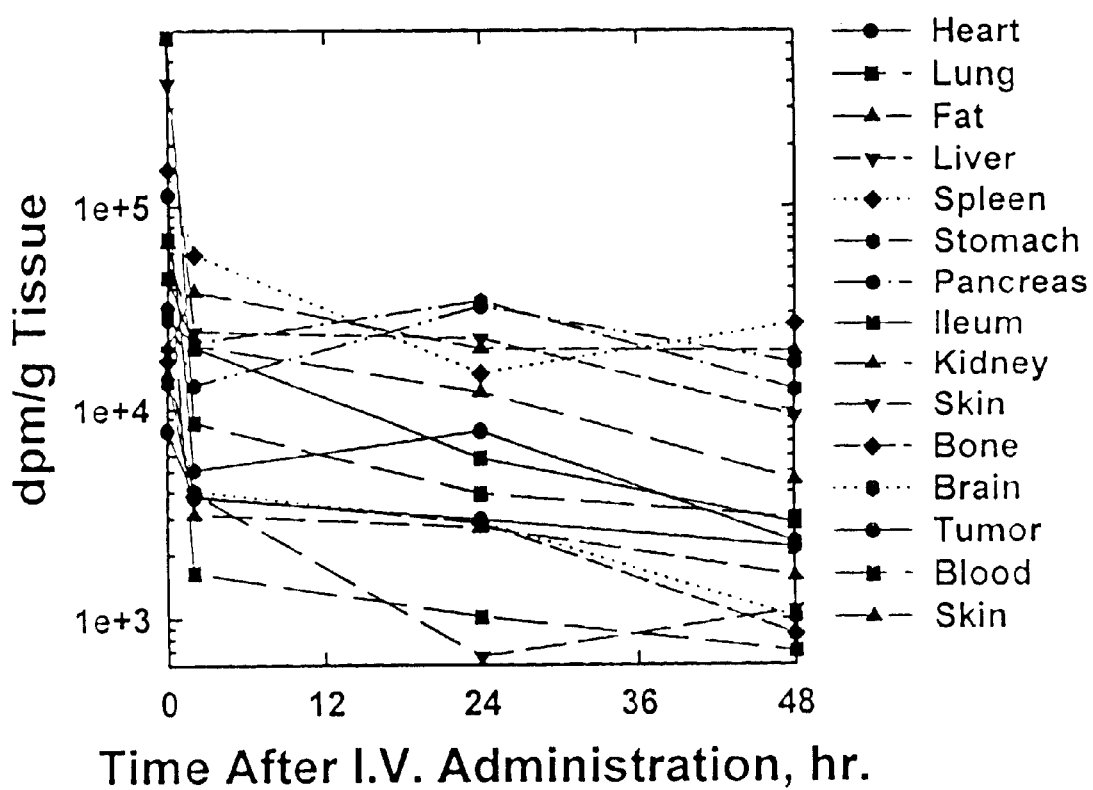
FIG. 6 shows the pharmacokinetics of $^{14}$C-HB in Balb/c mice bearing the EMT6/Ed tumor in one flank.

Pharmacokinetics of $^{14}$C-HB in Balb/c mice bearing the EMT6/Ed tumor in one flank. The results are shown in FIG. 6. Note rapid clearance of HB from blood. With respect to skin, the optimal therapeutic ratio for tumor occurs 2 hours following drug administration.

Example 7

EMT6/Ed tumor control in Balb/c mice following various doses of 630 nm light applied transcutaneously. The results are shown in FIG. 7. HBEA-R1 was administered at a fixed dose. True control represents animals given neither photosensitizer nor laser light. The animals were treated approximately 7 days following tumor implantation, and euthanized when tumors reached four times treatment volume.

Example 8

Sonodynamic toxicity of two perylenequinone derivatives in human promyelocytic leukemia cells in vitro, with respect to a positive control, hematoporphyrin at 1 mM. The results are shown in FIG. 8. The two compounds, for which the structures are shown, exhibit dose-dependent cell killing, and an excellent sonosensitizing efficiency.

with tone-burst and pulsed ultrasound. They observed significant ultrasound-induced increases in drug cytotoxicity in vitro in two of the three cell lines they used. Testing of the sonodynamic activity of these drugs in vivo showed significant antitumour effect as measured by volume reduction in uterine cervical squamous cell carcinomas in Syrian hamsters (Harrison et al., 1991). The molecular basis of the sonodynamic effect of doxorubcin was also examined by

TABLE 1

Physical and Chemical Properties for Hypocrellins

| Name of Compound | | Chemical Formula | F.W. | Abs. Peak in red Spectral region (nm) | $A_{max}$/solvent | $A_{630}$ | Extinction Coefficient ($\times 10^{-3}$) (630 nm) | $^1O_2$ Yield | $LD_{50}$ Dark ($\mu M$) | $LD_{50}$ Light ($\mu M$) | Photo-potentiation Factor |
|---|---|---|---|---|---|---|---|---|---|---|---|
| HA | Hypocrellin A | $C_{30}H_{26}O_{10}$ | 546 | 658* | 0.093/DMF | 0.086 | 0.86 | 0.84 | 15 | 3–5 | 3–5 |
| HB | Hypocrellin B | $C_{30}H_{24}O_9$ | 528 | 658* | 0.118/DMF | 0.100 | 1.00 | 0.74 | 20 | 1.5–2 | 10–13 |
| HA-$Mg^{++}$ | HA-$Mg^{++}(Ac_2)$ | $C_{34}H_{28}O_{12}Mg$ | 652 | 616 | 0.958/EtOH | 0.447 | 4.47 | 0.71 | >25 | >5 | ND |
| HB-$Mg^{++}$ | HB-$Mg^{++}$ | $C_{34}H_{26}O_{11}Mg$ | 634 | 622 | 0.604/EtOH | 0.527 | 5.27 | 0.53 | 10 | 1 | 10 |
| DAHA | Deacetylated-HA | $C_{32}H_{24}O_{13}Mg$ | 592 | 622 | O.651/EtOH | 0.570 | 5.70 | 0.51 | >25 | >5 | ND |
| HBAC-R1 | Cystamine-HB | $C_{32}H_{27}O_8Mg$ | 585 | 646 | 0.417/$CHCl_3$ | 0.388 | 3.88 | 0.40 | 12.5 | 1 | 12.5 |
| HBAC-R2 | Cystamine-HB | $C_{32}H_{27}O_8Mg$ | 585 | 600 | 0.337/DMSO | 0.244 | 2.44 | 0.31 | 12.5 | 5 | 2.5 |
| HBBA-R2 | n-butylaminated HB | $C_{36}H_{60}N_1O_7$ | 780 | 616* | 0.628/$CHCl_3$ | 0.619 | 6.19 | 0.32 | >100 | 0.2–0.6 | 167–500 |
| HBAM-R1 | 2-morpholino-ethyl-aminated-HB | $C_{42}H_{48}N_4O_9$ | 752 | 658 | | | | 0.70 | >25 | 4 | >6.25 |
| HBDD-R2 | 2-(N,N-diethyl-amino) ethylamine-HB | $C_{42}H_{52}N_4O_7$ | 696 | 646* | 0.508/$CHCl_3$ | 0.055 | 0.55 | 0.36 | >25 | 7.5 | >3.3 |
| HBDP-R1 | 2-(N,N-dimethyl-amino) propylamine-HB | $C_{40}H_{48}N_4O_7$ | 724 | 640* | 0.463/$CHCl_3$ | 0.480 | 4.80 | 0.42 | >25 | 0.5–1.5 | >16.6–50 |
| HBEA-R1 | Ethanolamine-HB | $C_{34}H_{34}N_2O_9$ | 614 | 696* | 0.625/DMSO | 0.623 | 6.23 | 0.60 | 15–25 | 0.15 | 100–167 |
| HBEA-R2 | Ethanolamine-HB | $C_{34}H_{34}N_2O_9$ | 614 | 634* | 0.162/DMSO | 0.127 | 1.27 | 0.70 | 25 | 7.5 | 3.3 |
| HBED-R2 | Ethylenediamine-HB | $C_{38}H_{32}N_8O_6$ | 696 | 614* | 1.449/DMSO | 1.239 | 12.39 | 0.50 | >25 | 3–5 | 5–8.3 |
| HBMA-IV | Methylamine-HB | $C_{30}H_{33}N_3O_6$ | 696 | 640 | 0.246/$CHCl_3$ | 0.246 | 2.46 | 0.80 | 8.5 | 1 | 8.5 |
| DBHB | 5,8-dibromo-HB | $C_{30}H_{23}O_9Br_2$ | 531 | ND | ND | ND | ND | 0.62 | 10 | 3 | 3.3 |
| DMHB | demethylated HB | $C_{28}H_{16}O_9$ | 686 | 648* | 0.469/EtOH | 4.77 | 4.77 | 0.42 | >25 | 3–5 | >5–8.3 |
| JL-1-1 | | $C_{30}H_{36}O_{12}$ | 578 | 594 | 0.478/$CHCl_3$ | 0.062 | 0.62 | 0.72 | >70 | 2–4 | >18.5 |

HBBA-R2, HBDP-R1, HBEA-R1, and JL-1-1 demonstrate average or lower than average toxicity, with excellent potentiation. For the purposes of this study, the $LD_{50}$ light dose was not fixed. For the compounds tested, this dose is 0.75–1.0 J/cm2 of 630 nm light.
ND = not done.
*Significant light absorption at 630 nm.
F.W. = formula weight.

TABLE 2

Tissue Uptake of $^{14}$C-Hypocrellin B (dpm/g)

| Tissue | 0 Hours | 2 Hours | 24 Hours | 48 Hours |
|---|---|---|---|---|
| Heart | 113,920 ± 3,365 | 5,135 ± 910 | 7,835 ± 1,810 | 2,325 ± 245 |
| Lung | 651,100 ± 42,668 | 8,580 ± 655 | 3870 ± 525 | 2,975 ± 360 |
| Fat | 20,550 ± 715 | 38,570 ± 5,610 | 19,550 ± 2,210 | 19,335 ± 2,335 |
| Liver | 394,190 ± 7,540 | 24,620 ± 4,885 | 22,495 ± 4,440 | 9,215 ± 720 |
| Spleen | 151,870 ± 9,395 | 58,900 ± 4,205 | 14,970 ± 3,215 | 26,700 ± 11,105 |
| Stomach | 28,280 ± 145 | 21,630 ± 3,345 | 34,385 ± 8,795 | 12,460 ± 975 |
| Pancreas | 32,010 ± 2,165 | 13,185 ± 12,055 | 32,390 ± 11,840 | 16,915 ± 3,845 |
| Ileum | 45,400 ± 3,600 | 20,280 ± 2,850 | 5,800 ± 645 | 2,840 ± 595 |
| Kidney | 67,344 ± 950 | 20,855 ± 3,955 | 12,050 ± 1,845 | 4,535 ± 765 |
| Skin | 14,970 ± 74 | 3,130 ± 221 | 2,700 ± 170 | 1,590 ± 250 |
| Bone | 19,825 ± 2,300 | 3,955 ± 2,070 | 660 ± 215 | 1,125 ± 310 |
| Brain | 17,560 ± 560 | 3,855 ± 170 | 2,840 ± 275 | 845 ± 90 |
| Muscle | 13,665 ± 600 | 4,050 ± 940 | 2,875 ± 560 | 1,015 ± 205 |
| Tumor | 7,885 ± 270 | 3,775 ± 400 | 2,950 ± 80 | 2,165 ± 470 |
| Serum | 69,975 ± 1,925 | 1,655 ± 170 | 1,020 ± 160 | 700 ± 240 |

Example 10

The first compounds to have identifiable sonotoxic effects were certain existing chemotherapeutic agents (Umemura et al., 1990). In their investigation of potentiation of chemotherapeutic cell killing by low-level ultrasound, Harrison et al. found synergistic effects of doxorubicin and diaziquone with tone-burst and pulsed ultrasound. Umemura et al., who found that ultrasound-induced cell damage and nitroxide production with TMPone were closely related, and that both effects were inhibited by the addition of histidine. These results are consistent with a sonodynamic mechanism that is related to the ultrasound-induced production of active oxygen species and similar to that observed for Hp (Umemura et al., 1997).

The sonodynamic effect of a compound structurally related to doxorubicin, the fluorine-containing anthracycline derivative FAD104 (3'-deamino-2'-fluoro-3'-hydroxydoxorubicin-14-pimelate) was investigated in vitro by Yumita et al. Studies of sarcoma 180 cells insonated in the presence and absence of FAD 104 demonstrated that the rate of cell damage doubled in the presence of 80 $\mu$M FAD 104, while no cell damage was observed with FAD 104 alone. As with doxorubicin and Hp, the synergy between ultrasound and FAD 104 was significantly inhibited by histidine, again suggesting a sonotoxic mechanism related to the production of reactive oxygen species (Yumita et al., 1998). Pheophorbide A(Ph-A) has also been noted to possess synergistic cytotoxic effects in combination with ultrasound. Umemura et al. investigated the sonodynamic effect of Ph-A in vitro and in vivo on sarcoma 180 cells. The presence of 80 $\mu$M Ph-A was found to double the rate of ultrasound-induced cell damage. This was significantly inhibited by histidine, which suggests that this effect too was mediated by sonodynamically generated oxygen species. Studies in mice where 56 mg/kg Ph-A was administered before insonation, showed that ultrasound treatment completely inhibited tumor growth at an intensity at which ultrasound alone showed little antitumor effect (Umemura et al., 1996:*Sonodynamically Enhanced Effect of Pheophorbide A*).

A promising new sonosensitizer is a gallium-porphyrin complex, ATX-70 (2,4-bis(1-decyloxyethyl)-Ga(lll)-1,3,5,8-tetramethylporphryin-6,7-dipropionyl diaspartic acid). Enhancement of ultrasound-induced cell damage in vitro by ATX-70 was investigated by Umemura et al. Where 80 $\mu$M Hp was found to double the rate of ultrasound-induced damage to sarcoma 180 cells, ATX-70 at the same concentration increased the rate of damage in excess of four times. Addition of histidine was found to inhibit the sonodynamic effect, while addition of mannitol had no effect. This indicates that singlet molecular oxygen may be the principal mediator of the observed sonodynamic toxicity. EPR studies of insonated solutions of ATX-70 showed that the reaction of TMPone with active oxygen species produced levels of nitroxide 2.5 times greater than those produced by solutions containing Hp. Singlet oxygen production was confirmed by the bleaching of N,N-dimethyl-4-nitrosoaniline in the presence of imidazole. Comparable to the difference in nitroxide production, ultrasound induced bleaching was three times as great in the presence of ATX-70 as in the presence of Hp at the same concentration (Umemura et al., 1993).

Example 11

HL-60 cells were treated with perylenequinone sensitizers and insonated as described above. The surviving fractions were plotted against sensitizer concentration. At a concentration of approximately 30$\mu$M, CPMg(Ac$_2$) showed sonotoxicity exceeding that of the 1000 $\mu$M Hp control, with the decrease in survival occurring steeply over the preceding two decades of sensitizer concentration. DBHB and DMHB showed negligible sonotoxicity up to 100 $\mu$M; the bulk of the observed sonotoxic effect occurred over the decade from 100 $\mu$M to 1000 $\mu$M, and the maximum effect was comparable to that of the Hp control (FIG. 8). HBMg(Ac$_2$) showed no sonotoxic effect until 10 $\mu$gM. Cell survival decreased steeply over the next two decades of sensitizer concentration.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. A method of activating a pharmaceutical composition consisting of an amino hypocrellin compound which essentially consists in exposing the hypocrellin compound to ultrasound between about 50 kHz and about 3 MHz.

2. The method of claim 1 wherein the hypocrellin compound is selected from the group consisting of butylaminated hypoorellin B; 2-(N,N-dimethylamino)-propylamine-hypocrellin B; ethanolaminated hypocrellin B; and 1,1 2-Bis [2-(acetyloxy)propyl]-2,4,6,7,9,11-hexamethoxy-3,10-perylenedione.

3. The method of claim 1 wherein exposing the hypocrellin compound to ultrasound comprises exposing the compound to a frequency between about 1 MHz and about 3 MHz.

* * * * *